(12) United States Patent
Masumura (10) Patent No.: US 8,976,433 B2
(45) Date of Patent: Mar. 10, 2015

(54) APPARATUS AND METHOD FOR IRRADIATING A SCATTERING MEDIUM

(75) Inventor: Takahiro Masumura, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 35 days.

(21) Appl. No.: 13/328,255

(22) Filed: Dec. 16, 2011

(65) Prior Publication Data

US 2012/0182591 A1    Jul. 19, 2012

Related U.S. Application Data

(60) Provisional application No. 61/424,543, filed on Dec. 17, 2010.

(51) Int. Cl.
*G03H 1/12* (2006.01)
*G03H 1/04* (2006.01)
*G01N 21/00* (2006.01)
(Continued)

(52) U.S. Cl.
CPC .............. *G03H 1/0443* (2013.01); *G01N 21/00* (2013.01); *G01N 21/4795* (2013.01); *G01N 21/6456* (2013.01); *G02B 21/0032* (2013.01); *G02B 21/0052* (2013.01); *G02B 21/0056* (2013.01); *G02B 26/06* (2013.01); *G01N 2201/0675* (2013.01); *G03H 2001/0083* (2013.01); *G03H 2001/0447* (2013.01); *G03H 2001/0467* (2013.01)
USPC .............................................. 359/11; 359/10

(58) Field of Classification Search
CPC .............. G03H 1/0443; G03H 1/0005; G03H 2001/0033; G01B 11/2441; G01B 11/22; G01B 9/021; G01B 11/0675; G01B 9/02; G01N 21/453

USPC ......... 359/1–15, 130, 224, 295, 230, 573, 21, 359/34, 35, 902; 356/479, 490, 495, 511, 356/512, 457, 458, 477, 496–498
See application file for complete search history.

(56) References Cited

U.S. PATENT DOCUMENTS 4,284,324 A * 8/1981 Huignard et al. ................. 359/7
4,385,634 A   5/1983 Bowen
(Continued)

OTHER PUBLICATIONS

Zahid Yaqoob, Demetri Psaltis, Michael S. Feld, Changhuei Yang, Optical Phase Conjugation for Turbidity Suppression in Biological Samples, Nature Photonics, Jan. 27, 2008, 2(2):110-115, Nature Publishing Group, New York, NY, 2008.

(Continued)

*Primary Examiner* — Thomas K Pham
*Assistant Examiner* — Sharrief Broome
(74) *Attorney, Agent, or Firm* — Canon USA Inc IP Division (57) ABSTRACT

An apparatus includes a low-coherent light source configured to emit an electromagnetic wave; a spatial light modulator configured to modulate a wavefront of the electromagnetic wave; an interferometer including a movable mirror to set a depth of a medium to be irradiated by the electromagnetic wave and a beam splitter configured to the electromagnetic wave into a reference beam and an object beam; a detector to detect information about an interference pattern formed by the object beam coming from the medium via the beam splitter and the reference beam reflected by the movable mirror; and a controller configured to control the spatial light modulator, based on the information, to form a modulated wavefront for irradiating the medium.

12 Claims, 5 Drawing Sheets

(51) Int. Cl.
*G01N 21/47* (2006.01)
*G01N 21/64* (2006.01)
*G02B 21/00* (2006.01)
*G02B 26/06* (2006.01)
*G03H 1/00* (2006.01)

(56) References Cited

U.S. PATENT DOCUMENTS

| | | | |
|---|---|---|---|
| 5,424,843 A | 6/1995 | Tromberg et al. | |
| 5,441,054 A | 8/1995 | Tsuchiya | |
| 5,477,051 A | 12/1995 | Tsuchiya | |
| 5,517,987 A | 5/1996 | Tsuchiya | |
| 5,713,356 A | 2/1998 | Kruger | |
| 5,840,023 A | 11/1998 | Oraevsky | |
| 6,738,653 B1 | 5/2004 | Sfez et al. | |
| 7,460,248 B2 * | 12/2008 | Kurtz et al. | 356/521 |
| 2007/0285751 A1 * | 12/2007 | Kim | 359/10 |
| 2008/0037367 A1 | 2/2008 | Gross et al. | |
| 2009/0009834 A1 | 1/2009 | Yaqoob et al. | |
| 2009/0051988 A1 * | 2/2009 | Sasaki et al. | 359/3 |

OTHER PUBLICATIONS

Vellekoop, M. I, et al., "Focusing coherent light through opaque strongly scattering media", Optics Letters 32(16), 2309-2311 (2007), The Netherlands.

Vellekoop, M. I, et al. "Demixing light paths inside disordered metamaterials" Optics Express 16, 67-80 (2008), The Netherlands.

* cited by examiner

APPARATUS AND METHOD FOR IRRADIATING A SCATTERING MEDIUM

CROSS REFERENCE TO RELATED APPLICATION

This application claims priority to U.S. provisional application No. 61/424,543 filed Dec. 17, 2010 entitled "Irradiation Method With Low Coherence Light for Delivering Light Inside a Scattering Medium". The whole of the provisional application is incorporated by reference herein.

BACKGROUND OF THE INVENTION

1. Field of the Invention

The present invention relates to an apparatus and a method for irradiating a scattering medium.

2. Description of the Related Art

Vellekoop et al. demonstrated that focusing light through scattering medium is possible by controlling the incident wavefront with spatial light modulator (SLM) and their phase optimization algorithm (Vellekoop, I. et al, Opt. Lett. 32(16), 2309-2311 (2007)). They infer an optimal incident wavefront in such a way that the target intensity monitored by a CCD becomes highest at given segment (pixel) on the SLM by cycling its phase from 0 to $2\pi$. Once they finished optimizing the wavefront, the incident light which has the optimized wavefront can focus light at a CCD plane.

Focusing light just after passing through a scattering medium is possible by controlling the wavefront of the incident light with the SLM. The position of the focus point obtained by this technique, however, is not inside the scattering medium but behind the medium where light is transmitted.

Vellekoop et al. further disclosed the way to focus light inside the scattering medium where a fluorescence probe lies (Vellekoop, I. et al, Opt. Express 16, 67-80 (2008)). The focused light intensity can be monitored by a CCD and control a SLM to optimize the incident wavefront for focusing. However, positions of fluorescence probes in a sample cannot be controlled.

SUMMARY OF THE INVENTION

Embodiments of the present invention provide an apparatus and a method for irradiating a scattering medium.

According to an aspect of the present invention, it is provided that an apparatus includes a low-coherent light source configured to emit an electromagnetic wave; a spatial light modulator configured to modulate a wavefront of the electromagnetic wave; an interferometer including a movable mirror to set a depth of a medium to be irradiated by the electromagnetic wave and a beam splitter to split the electromagnetic wave into a reference beam and an object beam; a detector to detect information about an interference pattern formed by the object beam coming from the medium via the beam splitter and the reference beam reflected by the movable mirror; and a controller configured to control the spatial light modulator, based on the information, to form a modulated wavefront for irradiating the medium.

According to another aspect of the present invention, it is provided that a method for irradiating a scattering medium includes: preparing a low-coherent light source to emit an electromagnetic wave; splitting the electromagnetic wave into a reference beam and an object beam; irradiating the scattering medium with the object beam to receive a signal light from the scattering medium; setting an optical path of the reference beam; impinging the signal light and the reference beam onto a holographic material to record an interference pattern formed by the signal light and the reference beam; impinging a pumping light onto the holographic material to generate a phase conjugate wave of the signal light; impinging the phase conjugate wave onto the scattering material; and detecting a signal light coming from the scattering medium due to the phase conjugate wave.

Further features of the present invention will become apparent from the following description of exemplary embodiments with reference to the attached drawings.

DESCRIPTION OF THE EMBODIMENTS

Embodiments according to the present invention will be described below with reference to the attached drawings.

Figure 1:
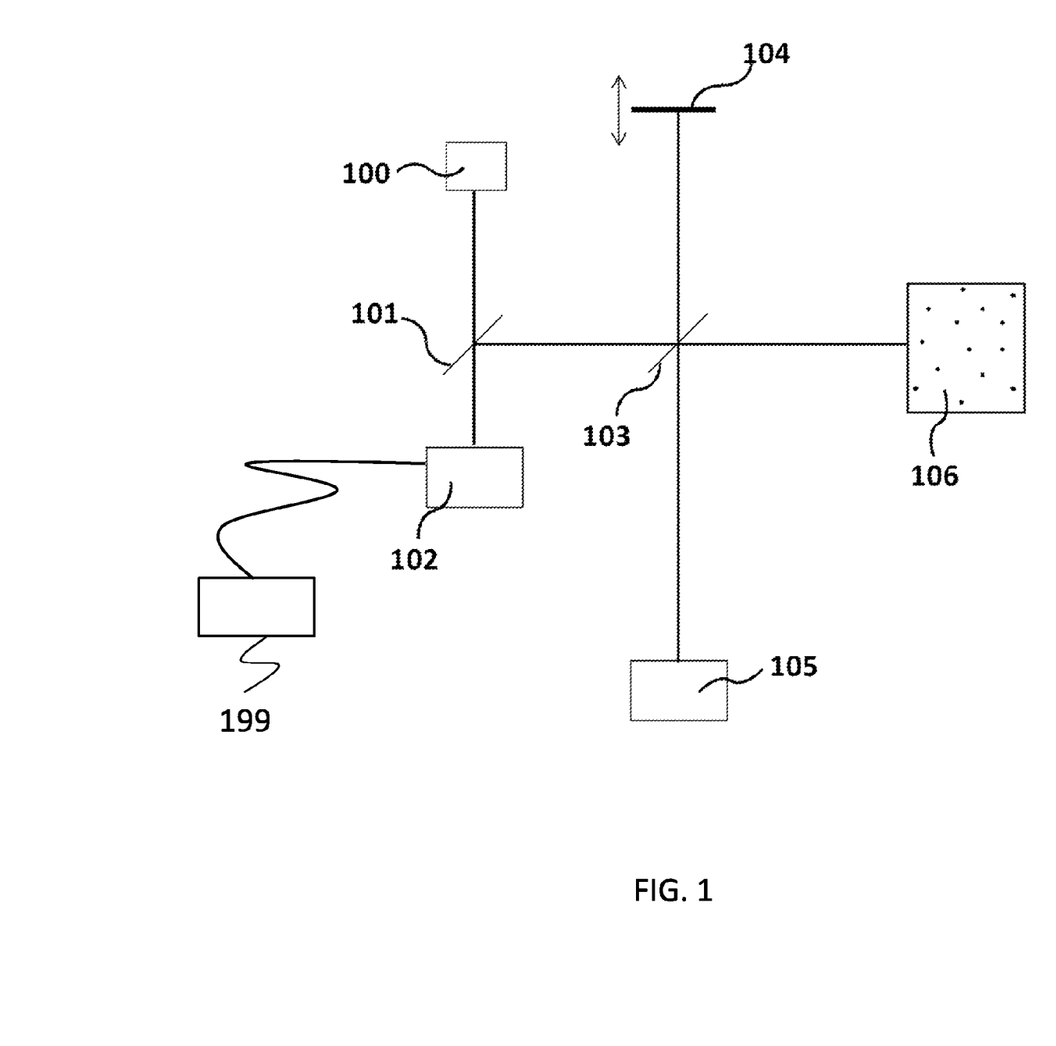
FIG. 1 illustrates an exemplary configuration of the irradiating apparatus.

FIG. 1 illustrates an exemplary configuration of the irradiating apparatus as a first embodiment. The apparatus is based on Michelson interferometer configuration. A low-coherent light source 100, such as a super luminescent diode (SLD) or amplified spontaneous emission source (ASE source), emits continuous-wave light as an initial light. The wavelength of the light emitted by the light source 100 can range from visible light to near-infrared light. For example, the wavelength can be selected from about 380 nm to about 2500 nm, such as from 400 nm to 1500 nm.

The initial light impinges onto a spatial light modulator (SLM) 102, such as a liquid crystal on silicon (LCOS) or a digital micro-mirror device (DMD), via a beam splitter 101. The SLM 102 changes phases of a wavefront of incoming initial light according to a measured result described below. The spatially modulated initial light is led to a beam splitter 103 where the initial light beam is split into an incident light beam (object beam) and a reference light, via the beam splitter 101.

The incident light beam goes into a scattering medium 106. Here, the scattering medium 106 can be, for example, a biological tissue or any other turbid medium or disordered material. In the scattering medium 106, the incident light is scattered as it propagates. Some portion of the light is scattered back as signal light and exits from the scattering medium 106, and recombined by the beam splitter 103 with the reference beam, of which path length is adjusted by a reference mirror 104. These two beams are received by a detector 105 comprising a CCD sensor. Here, a CMOS sensor or area sensors with an image intensifier, or EMCCD (Electron Multiplying CCD) are also applicable.

The signal light and the reference light coherently interfere each other only when their optical path lengths are matched within the coherence length of the light source 100. A length of a path of the reference light determined by the position of the mirror 104, which is movable, may be chosen for a particular transverse section (depth) of the scattering medium 106 that is to be irradiated and eventually may be imaged.

The phase and amplitude information of the signal light can be obtained from the interferogram (or digital hologram) by using phase shifting holography technique. The processing unit (not shown) may digitally reverse the measured wavefront and accordingly sets the phase value of each pixel in the SLM 102 to generate the reconstructed light which may be a phase conjugate of the signal light in the following irradiating process. The processing unit can be included in a controller 199 which is configured to control the SLM.

The above-described recording process is followed by an irradiating process. In the irradiating process, the initial light emitted by the light source 100 impinges onto the SLM 102 where its wavefront is modulated based on the phase values derived in the recording process. This phase modulation by the SLM 102 develops a reconstructed light which, may be the phase conjugate, is configured to irradiate the scattering medium 106. Because of the time-reversible nature of the phase conjugate, the reconstructed light can retrace its trajectory in the scattering medium 106 back to the certain depth determined by the reference arm in the recording process.

At this time, the difference of the optical length between the CCD 105 and the SLM 102 to the scattering medium 106 or any other system error may be calibrated, and the phase values may be corrected. Alternatively, the CCD 105 and the SLM 102 may be arranged so that the optical length from the exit plane of the medium 106 to those devices is the same. If the CCD 105 has a larger number of pixels compared to the SLM 102, the CCD 105 may perform binning so that the number of pixels between them is equal and those pixels are corresponding with each other. As the detector, the CCD 105 can detect information about an interference pattern formed by the object beam coming from the medium via the beam splitter 103 and the reference beam reflected by the movable mirror 104.

Figure 2A:
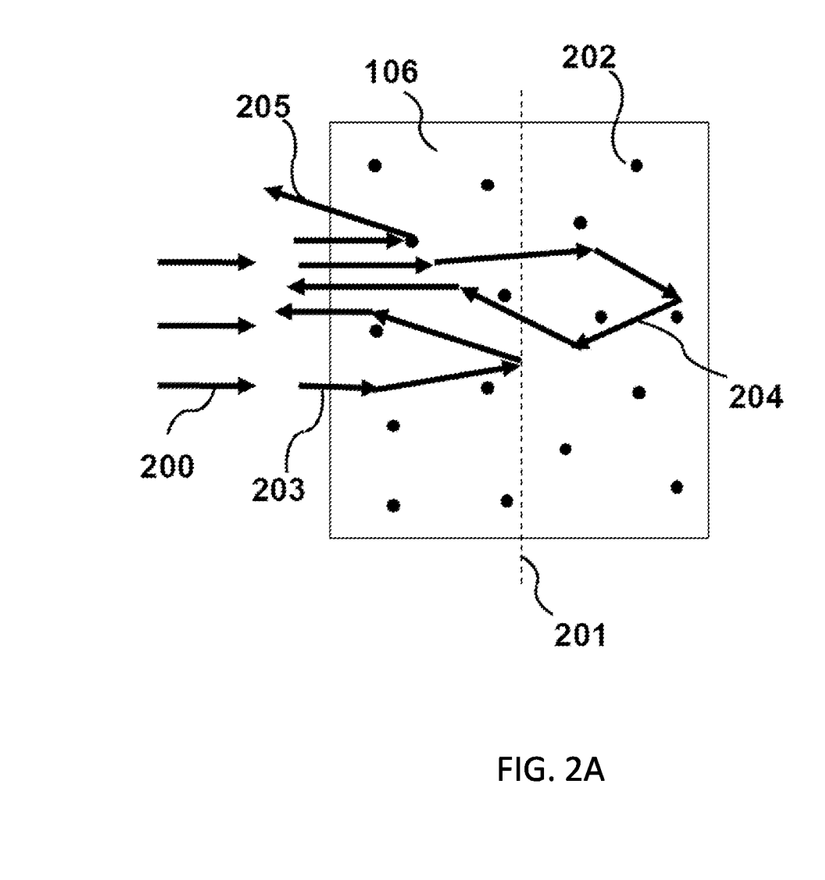
FIGS. 2A and 2B illustrate the propagation of the incident light in a scattering medium.
Figure 2B:
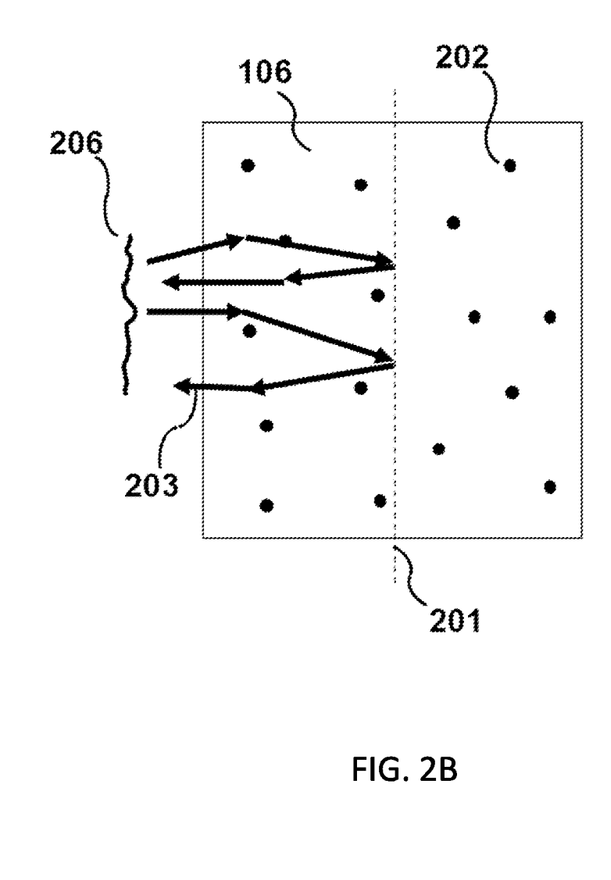

FIGS. 2A and 2B illustrate the propagation of the incident light at the recording process (FIG. 2A) and the propagation of the reconstructed light at the irradiating process (FIG. 2B). In the recording process, once the incident light 200 enters the scattering medium 106 including scatter particles 202, the light suffers scattering events. Some light 203 (signal light) travel at a specific depth 201 determined by the reference arm may be scattered back and exit the scattering medium 106 which coherently interfere with the reference light because of the same optical path length with the reference light. While some other light 204 or 205 may penetrate deeper or shorter than the light 203 in the scattering medium 106 and may be scattered back to exit the scattering medium 106, which may not contribute to the interferogram because the path length difference from the reference light is greater than the coherence length of the light source 100.

Therefore, the signal light 203 contributing to the interferogram obtained by the CCD 105 is originated from the specific depth section in the scattering medium 106. Because of the low coherence nature of the light source 100, the signal light 203 can be selectively recorded in the interferogram. By using digital holography technique, the wavefront of the signal light 203 may be obtained by the signal processing after the measurement. Since the phases assigned to the pixels on the SLM 102 are configured for generating the phase conjugate of the signal light 203 by reversing the measured wavefront of the signal light 203, the reconstructed light 206 may be equivalent to the phase conjugate of the signal light 203. Therefore, as shown in FIG. 2B, the reconstructed light 206 (i.e. the modulated wavefront) may retrace its original trajectory traveled in the recording process back to the specific depth section 201 and return to exit the scattering medium 106 in time-reversible way. Hence, it may be possible to enhance light delivery or concentrate the light to the specific depth section in the scattering medium by this technique. In addition, since the specific depth 201 is controllable by tuning the reference mirror 104, the target depth that is desired to be irradiated can also be controllable by the apparatus.

By delivering the light efficiently to the specific depth, it may be possible to enhance signal to noise ratio (SNR) of fluorescence imaging. After the recording process, a power of light with the phase conjugation, which is input into the medium for irradiating or imaging, can be different from that of the initial light used in the recording process. For this purpose, the low-coherence light source can have a power controller to change the power of the light. Optionally, a light source for the recording process can be different from a light source for the irradiating process or a imaging process.

The described method can be applied to depth-resolved fluorescence imaging which uses a chemical probe (molecule) to obtain biochemical information such as abnormality of the tissue for example. A configuration of a second embodiment is the same as the apparatus of the FIG. 1. As already described above, through the recording process, the phase distribution on the SLM 102 to deliver the light to a specific depth in the scattering medium 106 can be obtained.

In the irradiating process in the first or second embodiment, the reconstructed light may effectively be delivered to the specific depth section. Here, the power of the reconstructed light may be different from that of the initial light used in the recording process. The light source 100 can have a power controller to change a power of the light emitted from the source. Furthermore, a different type of the laser can be used such as pulse laser depending on the application such as for example, fluorescence life time imaging.

Figure 3:
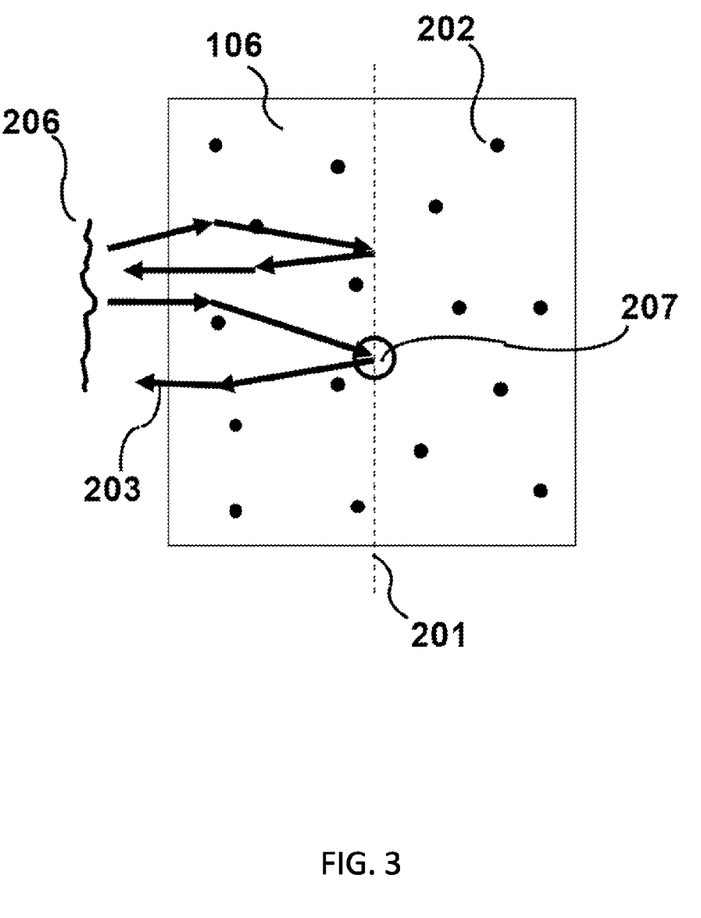
FIG. 3 illustrates a fluorescence probe in the scattering medium.

The reference mirror 104 may scan the probing (irradiating) depth 201 in FIG. 2A toward the deeper area bit by bit. Each time the scattered wavefront may be recorded through the recording process and followed by the irradiating process to effectively deliver the light to the specific probing depth. A bandpass filter (not shown) may be inserted in front of the CCD 105 to selectively detect the fluorescence signal which has different wavelength from the irradiating light. As shown in FIG. 3, when the probing depth is matched with the depth where the fluorescence probe 207 locates, the CCD 105 may detect the largest fluorescence signal. At the same time, the depth of the fluorescence probe can be estimated.

Since this is based on depth-resolved recording and irradiating process, the obtained largest signal intensity of the fluorescence by the CCD 105 may be transverse section image at the specific depth where the fluorescence probe locates. Because of the high efficiency to deliver the light power to the fluorescence, it may be possible to obtain high SNR fluorescence cross-section images in the scattering medium 106.

In addition, it may be possible to use a laser with low spatial-coherence illumination as a light source to obtain low coherence interferogram by using for example, rotating diffuser or microlens array.

Figure 4A:
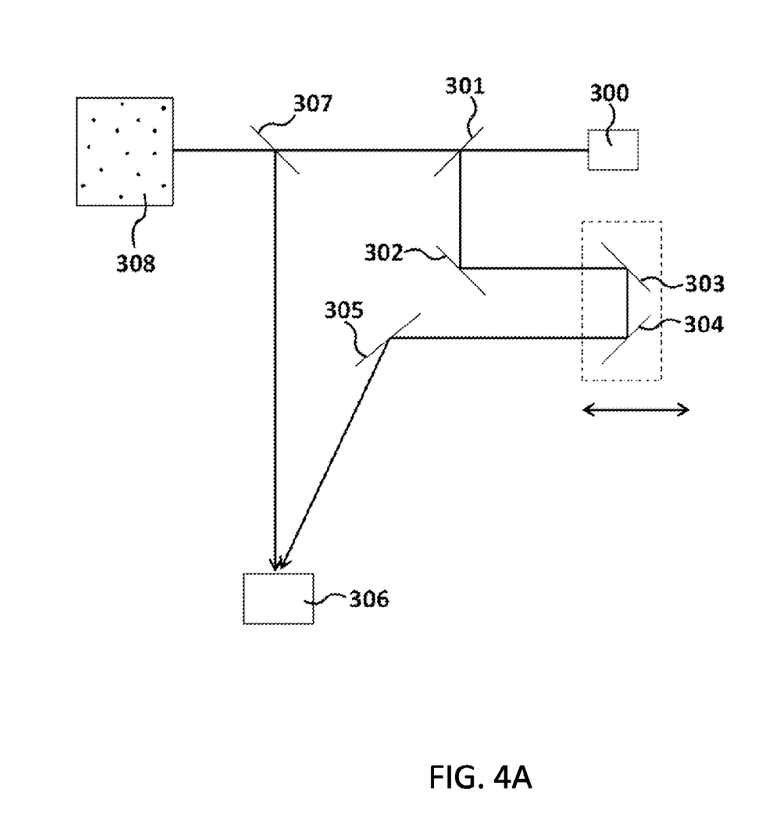
FIG. 4A illustrates a configuration for a recording process.

Alternatively, instead of using digital holography technique, this technique may be achievable by using holographic material, such as photorefractive crystal or photorefractive polymer. FIG. 4A illustrates a configuration of the recording process (step 1) as a third embodiment.

A low-coherent light source 300 emits light (an electromagnetic wave) as an initial light. The initial light is split into an incident light (an object beam) and a reference light (a reference beam) by a beam splitter 301. The incident light enters a scattering medium 308 through the beam splitters 301 and 307. In the scattering medium 308, the light suffers scattering events and some portion of the light (signal light) scattered backward exiting from the medium 308 is led to a photorefractive medium 306 via the beam splitter 307. The scattering medium is irradiated with the object beam to receive a signal light from the scattering medium.

The path length of the reference light is adjusted and set through reference mirrors 303 and 304. The reference light also impinges onto the photorefractive medium 306 at certain angle, through the mirrors 302, 303 and 304, controlled by a mirror 305 to interfere with the signal light to inscribe a hologram inside the photorefractive medium 306. The signal light and the reference beam are impinged onto the holographic material to record an interference pattern formed by the signal light and the reference beam.

As already described, because of the low-coherence of the light source 300 (e.g. SLD), the depth-resolved holography (interferogram) is generated in the photorefractive medium 306 in this recording process.

Figure 4B:
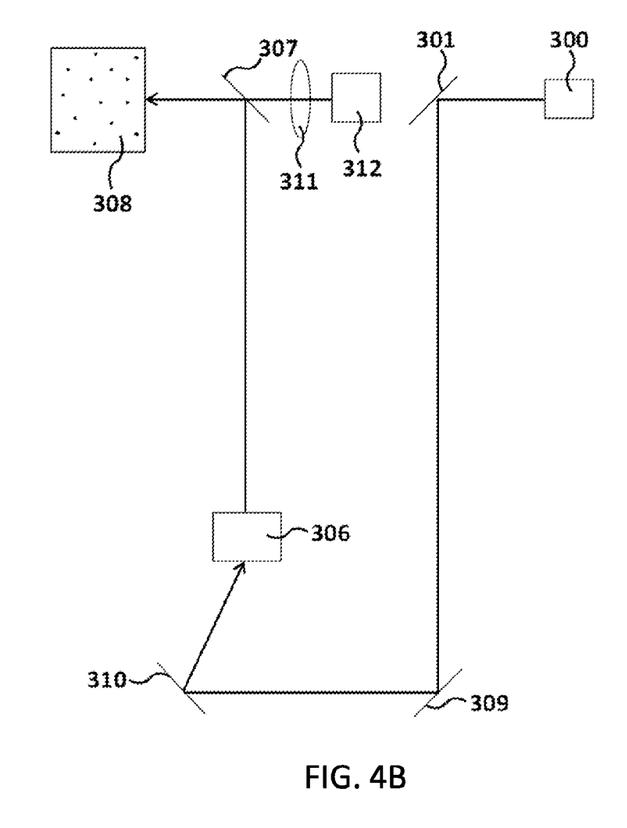
FIG. 4B illustrates a configuration for an irradiating process.

FIG. 4B shows an irradiating and following imaging process (step 2). A pumping light emitted by the same light source 300 is led to the beam splitter 301 working as a mirror, and the mirrors 309 and 310 to generate a phase conjugate of the signal light at the photorefractive medium 306. The reconstructed light may be configure to propagate toward the scattering medium 308 via the beam splitter 307 working as a mirror, and may retrace its trajectory to the specific depth section in the scattering medium 308, and exits from the scattering medium 308. A lens system 311 collects those exiting light and can be imaged by a CCD sensor 312. Instead of the CCD sensor, photo-detectors such as CMOS can be used.

In the scattering medium 308, some of the light may be lost due to the absorption or the scattering toward the direction which the photorefractive medium 306 cannot receive. As a result, the imperfect interferogram may be recorded and imperfect reconstructed light may be generated in the irradiating process. This imperfection as compared to the original incident light can be used to evaluate the absorption and scattering properties of the scattering medium 308.

The CCD 312 may acquire whole two-dimensional sectional image of those imperfections at the specific depth in the scattering medium 308. By adjusting the reference mirrors 303 and 304 to record different depth-resolved holograms, three-dimensional depth-resolved images may be obtained in the recording and irradiating processes. The following reference is hereby incorporated by reference in its entirety as though fully and completely set forth herein: U.S. Patent Application Publication No. 2009/0009834 to Yaqoob et al., published Jan. 8, 2009. In addition, the following are hereby incorporated by reference in their entireties as though fully and completely set forth herein: U.S. Pat. No. 6,738,653 to Sfez et al, issued May 18, 2004, and U.S. Patent Application Publication No. 2008/0037367 to Gross et al, published Feb. 14, 2008.

As to the imaging by using the optimized wavefront or the phase conjugate wavefront, the following are hereby incorporated by reference in their entireties as though fully and completely set forth herein: U.S. Pat. No. 5,441,054 to Tsuchiya, issued Aug. 15, 1995, U.S. Pat. No. 5,477,051 to Tsuchiya, issued Dec. 19, 1995, U.S. Pat. No. 5,517,987 to Tsuchiya, issued May 21, 1996, and U.S. Pat. No. 5,424,843 to Tromberg et al, issued Jun. 13, 1995. The following are hereby incorporated by reference in their entireties as though fully and completely set forth herein: U.S. Pat. No. 4,385,634 to Bowen, issued May 31, 1983, U.S. Pat. No. 5,840,023 to Oraevsky et al, issued Nov. 24, 1998, and U.S. Pat. No. 5,713,356 to Kruger, issued Feb. 3, 1998.

There might be an issue regarding the methods that utilize the phase conjugation to see through a scattering medium or focus light inside a scattering. That is a movement of scatterers. The technique described above is based on an assumption that the scatterers do not move throughout the process that includes recording and reconstructing (irradiating) steps. If the positions of the scatterers are different between the recording and the reconstructing steps, the phase conjugation is not "optimized irradiation" to focus light in a scattering medium. Although the movement of the scatterers is an issue to focus light, the decay of the optimized wavefront or phase conjugation provides with useful information regarding movement of scatterers that might be related to diagnostic information if the scattering medium is a living tissue such as blood flow.

Figure 5:
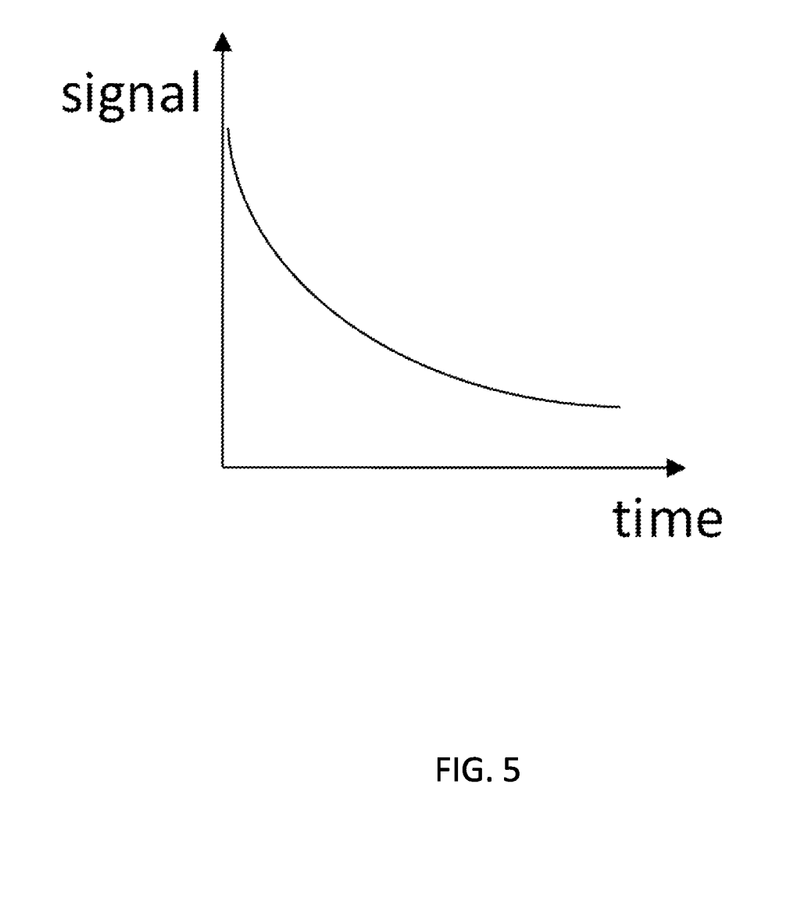
FIG. 5 illustrates a variation of a signal detected by a detector.

The optimized wavefront can focus on a local volume determined by the confocal system. Therefore, if the irradiation is followed by optical signal measurement, the obtained signal may be maximum just after the recording process due to the optimized incident light. However, because of the movement of scatterers, the optimized wavefront becomes less and less optimized as time advances. As a result, the obtained signal decreases with time as shown in FIG. 5.

The signal may be measured as a function of time with fixed phase conjugation obtained by the first step of either recording hologram. This decay reflects the speed of scatterers in the scattering medium. If the scatterers move very fast, the signal decays very rapidly. On the other hand, if the scatterers move very slow, the signal decays slowly. From this measurement, the information as to the flow of the scatterers may be extracted. Information about the decay of the signal can be displayed on a display to show a user.

The signal described above might be a photoacoustic signal, an acousto-optical signal, or a fluorescent signal (if a chemical probe is used) instead of light signal obtained by confocal system that utilizes this irradiating method. By monitoring the signal obtained by an imaging system with this irradiation apparatus, this additional information regarding the scattering property of the medium may be obtained.

While the embodiments according to the present invention have been described with reference to exemplary embodiments, it is to be understood that the present invention is not limited to the above described embodiments. The scope of the following claims is to be accorded the broadest interpretation so as to encompass all such modifications and equivalent structures and functions.

What is claimed is:

1. An apparatus comprising:
   a low-coherent light source for recording configured to emit an electromagnetic wave for recording;
   a mirror which is movable;
   a beam splitter configured to split the electromagnetic wave for recording into a reference beam heading for the mirror and an object beam heading for a medium;
   a detector configured to detect an interference pattern formed by the object beam coming from the medium and the reference beam reflected by the mirror;
   a light source for irradiation configured to emit an electromagnetic wave for irradiation; and
   a spatial light modulator configured to modulate a wavefront of the electromagnetic wave for irradiation by using information about the interference pattern detected by the detector, so as to irradiate the medium with an electromagnetic wave for irradiation having the modulated wavefront, wherein the mirror is configured to adjust an optical path length of the reference beam between the beam splitter and the detector, so as to set a specific depth inside the medium by matching the optical path length of the reference beam between the beam splitter and the detector with an optical path length of the object beam originated from the specific depth inside the medium between the beam splitter and the detector, wherein the spatial light modulator modulates the electromagnetic wave for irradiation into a phase conjugation wave of the object beam originated from the specific depth inside the medium by using the information, and wherein the phase conjugation wave travels back to the specific depth inside the medium set by the mirror.

2. The apparatus according to claim 1, wherein the low-coherent light source for recording is comprised of a super luminescent diode.

3. The apparatus according to claim 1, wherein the low-coherent light source for recording and the light source for irradiation are same light sources.

4. The apparatus according to claim 1, wherein the low-coherent light source for recording and the light source for irradiation are different light sources.

5. The apparatus according to claim 1, further comprising
a processing unit configured to generate an image using a signal generated by using the phase conjugation wave of the object beam originated from the specific depth inside the medium.

6. The apparatus according to claim 1, further comprising
a processing unit configured to generate an image using a photoacoustic signal generated by using the phase conjugation wave of the object beam originated from specific depth inside the medium.

7. An apparatus comprising:
a low-coherent light source for recording configured to emit an electromagnetic wave for recording;
a mirror which is movable;
a beam splitter configured to split the electromagnetic wave for recording into a reference beam heading for the mirror and an object beam heading for a medium;
a holographic material configured to record an interference pattern formed by the object beam coming from the medium and the reference beam reflected by the mirror; and
a light source for pumping arranged to irradiate the holographic material recording the interference pattern with an electromagnetic wave for pumping in a direction opposite to a direction of the reference beam, so that the holographic material generates a phase conjugation wave of the object wave, wherein the mirror is configured to adjust an optical path length of the reference beam between the beam splitter and the holographic material, so as to set a specific depth inside the medium by matching the optical path length of the reference beam between the beam splitter and the detector with an optical path length of the object beam originated from the specific depth inside the medium between the beam splitter and the detector, and wherein the holographic material generates the phase conjugation wave of the object beam originated from the specific depth inside the medium, which travels back to the specific depth inside the medium set by the mirror.

8. The apparatus according to claim 7, wherein the low-coherent light source for recording is comprised of a super luminescent diode.

9. The apparatus according to claim 7, wherein the low-coherent light source for recording and the light source for pumping are same light sources.

10. The apparatus according to claim 7, wherein the low-coherent light source for recording and the light source for pumping are different light sources.

11. The apparatus according to claim 7, further comprising
a processing unit configured to generate an image using a signal obtained by using the phase conjugation wave of the object beam originated from the specific depth inside the medium.

12. The apparatus according to claim 7, further comprising
a processing unit configured to generate an image using a photoacoustic signal obtained by using the phase conjugation wave of the object beam originated the from the specific depth inside the medium.

* * * * *